United States Patent [19]
Covino-Hrbacek et al.

[11] Patent Number: 5,604,438
[45] Date of Patent: Feb. 18, 1997

[54] CONTROLLED SPARK IGNITION TESTING APPARATUS

[75] Inventors: Josephine Covino-Hrbacek; Frank E. Hudson, III, both of Ridgecrest, Calif.

[73] Assignee: The United States of America as represented by the Secretary of the Navy, Washington, D.C.

[21] Appl. No.: 406,213

[22] Filed: Mar. 6, 1995

[51] Int. Cl.[6] .................................................. G01N 27/61
[52] U.S. Cl. .................... 324/464; 324/456; 324/536; 324/557
[58] Field of Search ................... 324/456, 455, 324/553, 554, 557, 464, 536

[56] References Cited

U.S. PATENT DOCUMENTS

| | | | |
|---|---|---|---|
| 3,601,694 | 8/1971 | Checketts et al. | 324/32 |
| 3,943,437 | 3/1976 | Mourier | 324/455 |
| 4,068,591 | 1/1978 | Betts | 102/70 |
| 4,620,145 | 10/1986 | Dietz | 324/456 |
| 4,663,585 | 5/1987 | Krüger et al. | 324/54 |
| 4,710,707 | 12/1987 | Knowles et al. | 324/158 |
| 4,760,341 | 7/1988 | Skerritt | 324/379 |
| 4,763,045 | 8/1988 | Choi et al. | 315/209 |
| 4,766,281 | 8/1988 | Bühler | 219/69 |
| 4,766,318 | 8/1988 | Adler-Golden et al. | 250/385.2 |
| 4,831,332 | 5/1989 | Rudisill | 324/455 |

*Primary Examiner*—Kenneth A. Wieder
*Assistant Examiner*—José M. Solis
*Attorney, Agent, or Firm*—Melvin J. Sliwka; John Forrest, Jr.

[57] ABSTRACT

A high voltage differential is applied across two separated electrodes by a voltage supply. Between these electrodes is located a sample of the solid propellant or other energetic material. The voltage differential across the electrodes generates a spark of measurable voltage, current and time duration in the sample in order to foretell at what energy level sustained ignition of the sample occurs. This spark is measured by a voltage monitor which, upon reaching a predetermined level, sends a signal to a short-circuiting network. The short-circuiting network, after a predetermined time delay, shorts the electrical path across the electrodes thereby removing the voltage differential across the sample and ending the ignition test. An operator is then able to determine visually whether or not the spark of known voltage, current and time duration has created sustained ignition of the sample material. With this information much can be ascertained about the electrostatic hazards of energetic material, thereby making the handling of these materials less dangerous.

14 Claims, 3 Drawing Sheets

CONTROLLED SPARK IGNITION TESTING APPARATUS

BACKGROUND OF THE INVENTION

This invention relates to an apparatus for creating, controlling and measuring electrostatic discharges in combustible materials, such as solid rocket fuel, in order to determine the charge necessary to create sustained ignition in these materials. In particular, the invention relates to a testing apparatus for controlling the duration of a spark applied to combustible materials.

The sensitivity of rocket propellants to electrostatic discharge (ESD) has been and is a major and continuing concern to the propulsion industry. The build-up and subsequent discharge of electrostatic charge on energetic materials used in ammunition and propulsion systems can pose a severe hazard during the handling of these systems. This hazard arises when energetic materials are charged to a potential where breakdown of the material occurs or when a change in grounding allows the breakdown of an existing charge in the material to occur. Discharge processes generate charge carriers, which in turn reduce the impedance of the energetic material and result in a rapid current increase. These processes can lead to arcing and the establishment and growth of discharged paths, followed by a catastrophic discharge. Such reactions lead primarily to pressure and temperature increases in very narrow discharge paths that may in turn induce ignition, sustained combustion or even detonation. Consequently, it is essential to predict a propellant's response to various levels of induced voltages and to study phenomena associated with electrostatic discharges in order to minimize the danger these discharges present to those working with energetic materials.

Being able to predict a propellant's response to given energy levels is important in assessing the ESD hazards of propellants and rocket motors. Tests used in the prior art, however, have the disadvantage of requiring considerable human judgment to assess the amount of damage caused to the sample by the ESD, thereby entering errors into the analysis of ESD hazards. These tests also may include energy delivered to the sample after ignition has occurred, causing errors in the determination of the sample's actual ignition point. Finally, the prior art tests may give erroneous results at high energy levels when the electrostatic discharge occurs over such a short period of time that the material is expelled before it has time to ignite.

SUMMARY OF THE INVENTION

Accordingly, it is an object of the present invention to provide an apparatus for testing the sensitivity of a solid propellant or other energetic material to electrostatic discharges with respect to the ignition point of the propellant.

It is further an object of this invention to provide a method for testing the electrostatic discharge sensitivity of energetic materials that eliminates, to a large extent, errors introduced by human judgment, by limiting this judgment to a simple yes or no determination of sample ignition.

It is still further an object of this invention to provide a testing apparatus for supplying a known quantity of current and voltage over a known period of time to a sample such that the exact ignition point of the sample can be determined without the inclusion of energy supplied to the material after ignition has begun.

It is also an object of this invention to provide an apparatus in which the amount and rate of energy delivered to the material is controllable and in which the sample material is securely held in the apparatus so as to assure that the material is not expelled during high energy tests.

The invention comprises an apparatus for testing energetic materials such as solid fuel propellants by creating, measuring and controlling spark discharges through a sample of the material. Means supplies a predetermined voltage. Means applies the predetermined voltage to the sample including two separated electrodes between which the sample is placed such that a voltage difference exists between said electrodes so as to induce a spark in the sample material. Means measures a parameter of the spark induced in the sample by the applying means. Means responsive to the measuring means controls the duration of the spark.

The invention also comprises a method for testing energetic materials such as solid fuel propellants by creating, measuring and controlling spark discharges through a sample of the material. The method comprises the steps of supplying a predetermined voltage; applying the predetermined voltage to the sample including two separated electrodes between which the sample is placed such that a voltage difference exists between said electrodes so as to induce a spark in the sample material; measuring a parameter of the spark induced in the sample by the applying means; and controlling the duration of the spark in response to the measuring means.

BRIEF DESCRIPTION OF THE DRAWINGS

The present invention will become more fully understood from the detailed description given below and the accompanying drawings which are given by way of illustration only, and which are not limitative of the present invention, wherein.

DETAILED DESCRIPTION OF PREFERRED EMBODIMENTS

Figure 1:
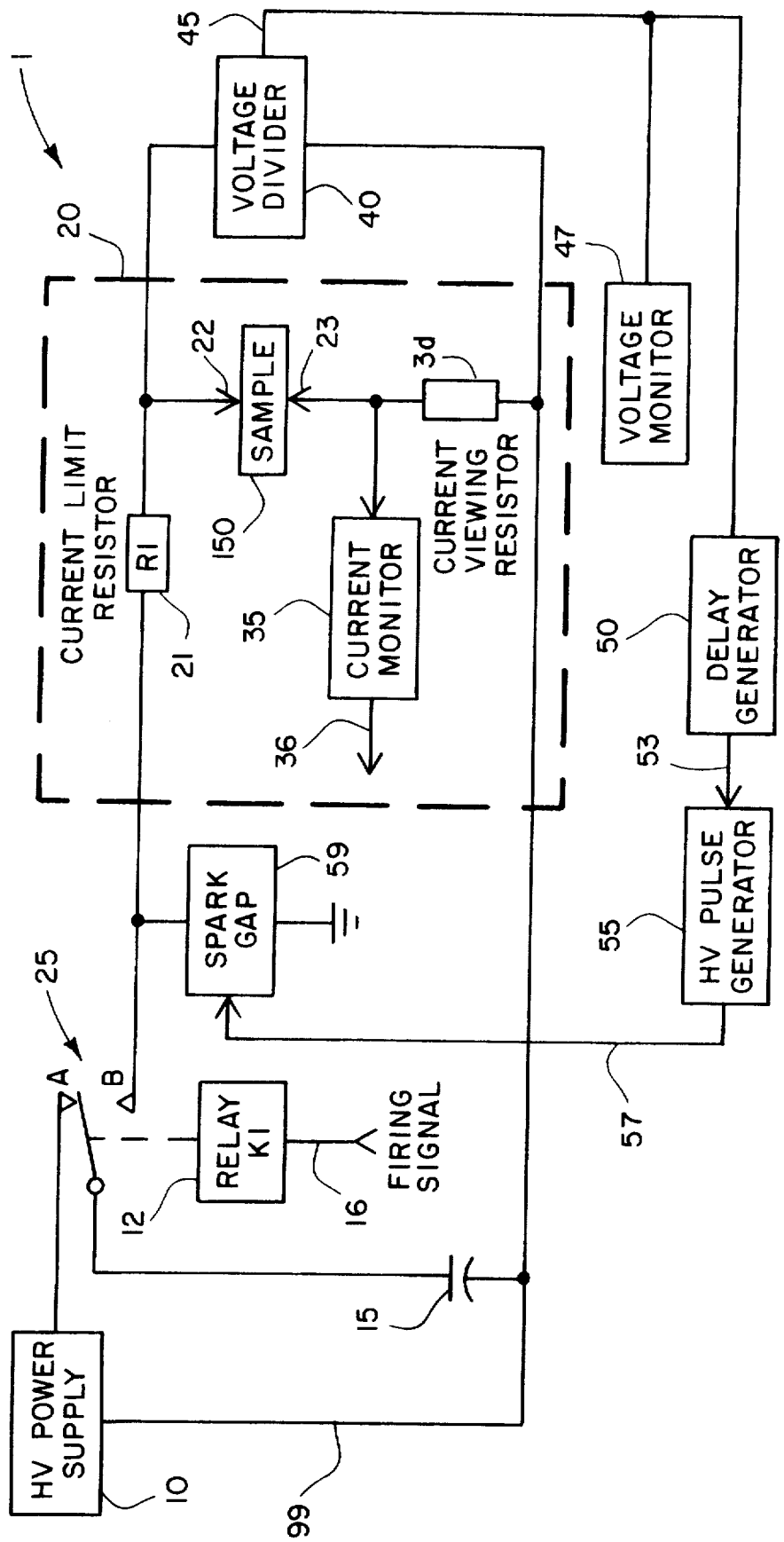
FIG. 1 is a circuit schematic of the preferred embodiment of the electrostatic discharge ignition testing apparatus.

Referring to FIG. 1, an electrostatic discharge generating, measuring and controlling circuit generally labeled 1 is shown wherein a high voltage power source 10 is connected through a switchable relay 12 to a storage capacitor 15. The relay 12, when in position A in its normally closed state, electrically connects the capacitor 15 to the high voltage power source 10. With the relay in this position, the capacitor 15 charges up to the voltage level of the voltage source 10.

At the start of a particular test, a firing signal (originating at an operator control panel not shown in the diagrams) energizes relay 12 on line 16, causing the relay to switch. This disconnects the capacitor 15 from the voltage source 10 and, after a delay equal to the switching time of the relay, moves to position B to connect the high voltage side of the capacitor 15 to a terminal 25 of the spark igniting circuit generally labeled 20. The capacitor 15 subsequently begins to discharge through the relay 12, supplying energy to the spark igniting circuit 20.

The spark igniting circuit 20 preferably comprises a current limiting resistor 21 connected in series to the normally open terminal 25 of relay 12. Limiting resistor 21 is connected to a first electrode 22 and a voltage divider 40. The current limiting resistor 21 limits the current supplied to the spark igniting circuit 20 by the capacitor 15 when the firing signal is present.

Figure 2:
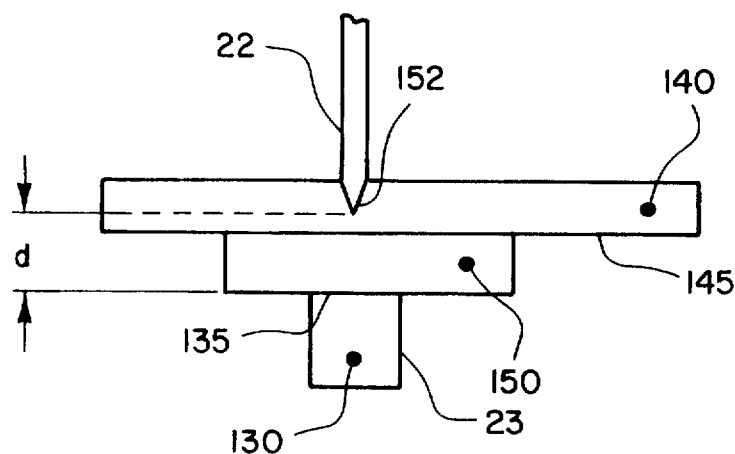
FIG. 2 is a mechanical drawing illustrating the preferred embodiment of the electrode configuration of the spark igniting circuit of the electrostatic discharge testing apparatus.

Referring now to FIG. 2, the electrode configuration generally labeled 28 consists of two electrodes 22 and 23, separated by a small distance, between which a sample material 150 is inserted for testing. The first electrode 22 comprises a vertically orientated bar, in this embodiment comprising a steel brad having a tapered end 152 terminating in a point located near or against the sample material 150. This tapered end is surrounded by and physically connected to a horizontally orientated plexiglass plate 140 having a flat horizontal surface 145 against which the sample material 150 rests. The tapered end 152 of the first electrode 22 is embedded in the plexiglass plate 140 and held in position thereby.

The plexiglass plate 140 eliminates gaps between the electrode and sample material in order to prevent arcing during testing of the material and supplies a flat surface 145 against which the sample material 150 will securely rest during testing. The purpose of the Plexiglass plate (140) is to confine the reaction area to the immediate vicinity of the steel brad (22), so that sparking in the sample occurs at a known location. The plate prevents ejection of sample material during the spark.

The second electrode preferably comprises an electrically conducting member designated 130, having a horizontally orientated surface edge 135 against which the sample material rests. The flat edges of the plexiglass plate and the second electrode are located in substantially parallel planes such that the sample material 150 can be placed between them, coming into contact with both surfaces 135 and 145 simultaneously, and thereby be held securely in the apparatus during testing. This configuration will prevent expulsion of the sample material during high energy tests.

When voltage is supplied by the capacitor 15 through relay 12 and current limiting resistor 21 a voltage differential, substantially dependent upon the voltage to which the discharging capacitor 15 has charged, arises between the two electrodes 22 and 23, more specifically across the gap between the tapered point of the first electrode 22 and the horizontal edge 135 of the second electrode 23. The high voltage being applied to the electrodes 22 and 23 generates an electrostatic discharge or spark across the gap between the electrodes 22 and 23 and through the sample material 150 held in this gap by the horizontally flat edges of the plexi-glass plate 140 and the second electrode 130. This discharge causes current to flow through the sample material. The amount of this current is dependent upon the value of the current limiting resistor and the internal resistance of the sample. The voltage differential of this generated spark is determined by the initial voltage of the discharging capacitor 15 and the current limiting resistor 21 while the duration of the spark is controlled by the delay means described in detail below.

Referring again to FIG. 1, connected in series with the electrode 23 as part of the spark igniting circuit 20 is a current viewing resistor 30. This current viewing resistor is usually very small in value so as not to dissipate excessive voltage and is used to determine the current passing through the sample material. The current viewing resistor 30 is connected between the bottom of the second electrode 23 and a common electrical line 99.

Connected in parallel with the current viewing resistor 30 is a current monitor 35 similar to any one of a number of such devices generally available off the shelf and known to one of ordinary skill in the art. A signal provided via output 36, representative of current flowing through resistor 30, is generated by the current monitor 35 and is continuously transmitted to a control panel (not shown) and saved as data by an information storing means (not shown) to enable an operator to determine the current flowing through the sample material 150 while the spark is being generated across the electrodes 22 and 23 of the spark igniting circuit 20.

Again referring to FIG. 1, connected in parallel with the electrodes 22 and 23 of the spark igniting circuit 20 and the current viewing resistor 30 is a voltage measuring means. In one preferred embodiment, the voltage measuring means includes a voltage dividing means 40 connected to voltage monitor 47. Voltage dividing means 40 is comprised of a network of two or more resistors connected in series with one another, with the high voltage side of the resistor network 40 connected between the first electrode 22 of the applying means 20 and the current limiting resistor 21 and with the low voltage side of the resistor network 40 connected to the common electrical line 99.

Connected at a point between two of the resistors of network 40 is a lead 45, which is connected to a voltage monitor 47 (described in more detail below) indicating the voltage across the resistors of the network connected between the lead 45 and the common electrical line 99. Alternatively, this resistor network and lead 45 could be replaced with a resistive potentiometer with the variable lead of the potentiometer preforming the function of the lead 45.

A voltage dividing resistive network 40 of the type described above, along with the current limiting resistor 21, will divide the voltage applied across the electrodes 22 and 23 such that the lead 45 will be at an electrical potential equal to a small percentage of the voltage across the electrodes 22 and 23. This avoids specialized and expensive measuring devices to measure the high voltages necessary to generate a spark across the sample. Such high voltages are also unsuitable to be used as triggering signals due to the damage they can cause to unprotected electrical components.

A voltage dividing network as described above will reduce the voltage being measured at lead 45 to a value that can be more conveniently utilized in measuring and controlling the operation of the electrostatic discharge generated between the electrodes 22 and 23 of the spark igniting circuit 20.

Voltage monitor 47 is connected to lead 45 and measures the voltage present at the lead 45 and is of a type generally available in the commercial market and known to those skilled in the art. The output of this voltage monitor 47 can be read manually by an operator or sent to a control panel (not shown in the drawings) to be stored for later use. The voltage across the electrodes 22 and 23 is determined from the voltage indicated by the voltage monitor 47 and the effective voltage division ratio of the voltage dividing resistor network 40. This information can be used to determine the voltage being applied to the sample material 150 during any given test.

Also connected to the terminal lead 45 is a delay pulse generator 50. This generator 50 upon receiving a signal from the voltage dividing resistor network 40 through the lead 45 will, after a delay of a preset amount of time, send a triggering voltage pulse to a spark terminating circuit. In particular, generator 50, which can be of the type generally available in the industry, is responsible for the timing of the spark induced across electrodes 22 and 23 and in the sample material 150. The delay of the pulse delay generator 50 essentially determines the spark duration in the sample material 150.

When relay 12 switches from position A to position B in response to a firing signal via line 16, the capacitor 15 begins discharging through the applying means 20 and the voltage dividing network 40. At this time the voltage dividing resistor network 40 instantaneously charges to the voltage level of the capacitor 15, sending a signal to the pulse delay generator 50 through line 45. This signal triggers the pulse delay generator 50 to begin timing delay. After the preset delay time of the generator 50, a signal is sent along line 53 which triggers short-circuiting means.

One preferred embodiment of the spark terminating circuit comprises a high voltage pulse generator 55 connected to a spark gap device 59 by line 57. The spark gap device 59 is connected in parallel with the capacitor 15 and spark igniting circuit 20 such that a short-circuit is created across the capacitor 15 and spark igniting circuit 20 where a spark is transmitted across the spark gap device 59. Upon receiving a triggering pulse from the delay pulse generator 50, the high voltage pulse generator 55, of the type available off the shelf and known to those skilled in the art, sends a high voltage pulse along line 57 to spark gap device 59. This pulse is of sufficient electrical potential to create a spark across the gap of the spark gap device 59. The spark across the spark gap device 59 creates a low resistive path, as seen by the discharging capacitor 15, which effectively short-circuits the capacitor 15 and the spark igniting circuit 20. Thus, when the spark occurs in the spark gap device 59, current stops flowing through the spark igniting circuit 20, thereby ending the electrostatic spark being applied to the sample material 150. Preferably, the current flow through the spark gap device 59 is much greater than the current flow through the electrodes 22, 23. The voltage pulse created by the voltage pulse generator 55 and applied to the spark gap device 59 is of long enough time duration to allow the capacitor 15 to completely discharge through the spark of the spark gap device 59. This assures that no energy is applied to the electrodes 22, 23 of the spark igniting circuit 20 after the spark gap device 59 has been triggered.

Figure 3:
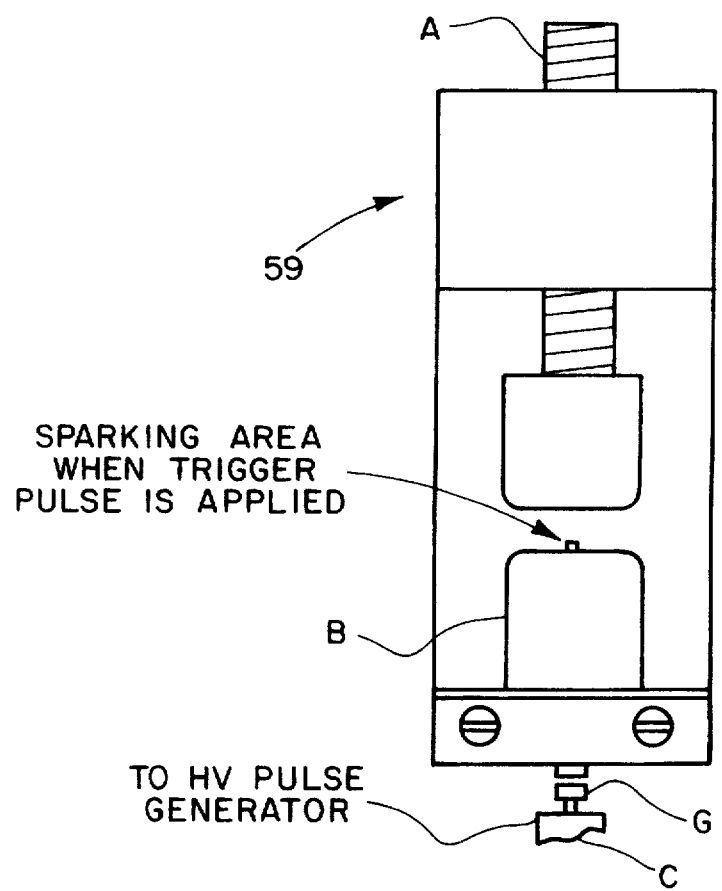
FIG. 3 is a schematic diagram of a spark gap device.
Figure 4:
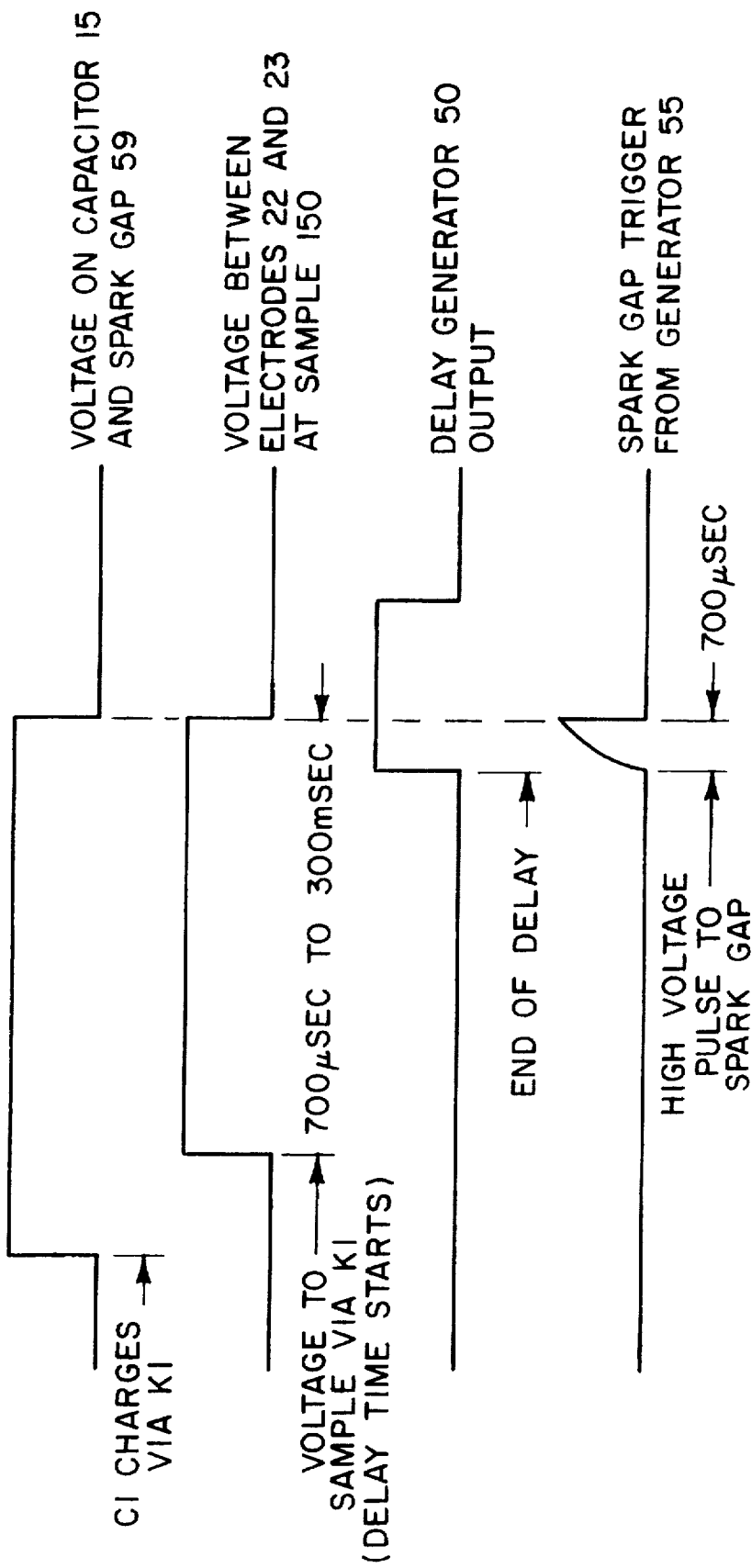
FIG. 4 illustrates waveforms on the capacitor 15, sample 150, delay generator 50, and HV pulse generator 53.

As shown in FIG. 3, the spark gap device 59 is a three terminal device. When a high voltage pulse is applied to trigger terminal C, which is surrounded by glass tube G, a small spark is formed between the end of C and the face of ground electrode B. The spark ionizes air near the surface of the ground electrode B thereby lowering the dielectric strength of the air between the high voltage electrode and the ground electrode. The lowered dielectric strength enables dielectric breakdown of the air between the high voltage electrode and the ground electrode. The breakdown is essentially a low resistance path (short circuit) between the high voltage terminal A and ground B. As shown in FIG. 4, the duration of the trigger pulse provided via line 57 by generator 55 is about 700 microseconds. The discharge time of the capacitor 15 is dependent on the series resistance. The voltage to the sample (with 1 Megohm series resistance) can be varied from 700 microseconds to 300 milliseconds.

When the voltage pulse sent to the spark gap device 59 by the high voltage pulse generator 55 is terminated, the spark in the spark gap device 59 will cease. Since the capacitor 15 is at this time completely discharged, there is no active energy source in the circuit. Therefore all circuit elements are at the same electrical potential and no current will flow.

At this time the sample material 150 can be removed either mechanically or by an operator from the gap between the electrodes 22, 23 of the spark igniting circuit 20. The sample material 150 can then be examined to determine if the spark transmitted by the electrodes 22, 23 during the test was of sufficient energy to create sustained ignition of the sample material 150. The operator makes a simple yes or no determination of whether the sample material 150 was ignited or not. Upon this determination the test can be modified by supplying more or less energy to the sample material in subsequent tests in order to more accurately determine the ignition point of the sample material 150.

An alternate embodiment of the spark terminating circuit includes a voltage controlled switch or relay in place of the spark gap device 59. This switch is connected in parallel with the spark igniting circuit 20 and the capacitor 15 such that upon receiving a voltage signal from the delay pulse generator 50, the switch closes and creates a short-circuit across the capacitor 15 and spark igniting circuit 20. This in turn halts current flow in the sample material. One disadvantage of such a switch configuration is that the switch takes more time to close than does the spark gap device 59 which may introduce uncertainty in the timing of the spark created in the sample material 150. A second disadvantage of such a switch configuration is that, due to the high voltages being used in the circuit, arcing may occur in the switch during operation, thereby causing damage to the switch and unreliable operation thereof.

In operation, before a test is begun, a sample of the energetic material 150 is inserted between the electrodes 22, 23 of the spark igniting circuit 20. The capacitor 15 is then charged by power supply 10 through relay 12 which is in its normally closed position A. When capacitor 15 is fully charged, a firing signal is sent to relay 12 on line 16 switching the relay 12 to its normally open position B. This disconnects capacitor 15 from the power supply 10 and connects it to the terminal 25 of the spark igniting circuit 20. Upon this switching, the capacitor 15 begins to discharge through the current limiting resistor 21, the electrodes 22, 23 of the spark igniting circuit 20 and the sample material 150. The current generated in the sample material 150 is determined by the voltage of the capacitor and the resistive values of the current limiting resistor 21 and the sample material 150. The voltage supplied by the capacitor 15 is measured by a voltage dividing resistor network 40. After being reduced to a suitable level by this network, the voltage provides a triggering signal to a delay pulse generator 50. Upon receiving this voltage triggering signal, the delay pulse generator 50 delays for a predetermined amount of time, thereby controlling the time duration of the spark in the sample material 150, before sending a triggering pulse to a high voltage pulse generator 55. The high voltage pulse generator 55 then sends a voltage pulse to the spark gap device 59 which is connected in parallel with the spark igniting circuit 20 and discharging capacitor 15. Due to this voltage pulse, a spark is generated across the spark gap device 59 which in turn creates a low resistive path for the discharging capacitor and shorts the electrodes 22, 23 of the spark igniting circuit 20, halting current flow through the sample material 150. Once the capacitor 15 has completely discharged through the spark of the spark gap device 59, the sample material 150 is removed from the circuit and examined. At this point the firing signal can be turned off, allowing the relay 12 to return to its normally closed position A. This in turn connects capacitor 15 to power supply 10, allowing it to recharge in preparation for the next test. The voltage and current flowing through the sample are measured and stored by the current and voltage monitors 35 and 47, respectively, with the timing of the test determined by the delay of the delay pulse generator 50.

In subsequent tests the energy transferred through the sample material 150 can be varied by changing the initial voltage level supplied to the capacitor 15 to provide a different voltage level across the electrodes 22, 23; by changing the current limiting resistor 21 to vary the current passing through the sample 150; or by changing the delay time of the pulse delay generator 50 to vary the time duration of the spark passing through the sample material 150. Multiple tests for each type of material may be necessary to determine the exact electrostatic ignition point of the material, i.e., the energy supplied to the material to cause ignition and no more.

The invention has been described in detail with particular reference to preferred embodiments thereof, but it will be understood that variations and modification can be effected within the spirit and scope of the invention.

What is claimed is:

1. An apparatus for testing energetic materials by creating, measuring and controlling spark discharges through a sample of the material, said apparatus comprising:

means for supplying a predetermined voltage;

means for applying the predetermined voltage to the sample including two separated electrodes between which the sample is placed such that a voltage difference exists between said electrodes so as to induce a spark in the sample material;

means for measuring a parameter of the spark induced in the sample by the applying means;

means responsive to the measuring means for controlling the duration of the spark; and the spark controlling means comprises means further connected in parallel with said applying means for short-circuiting said electrodes in response to the measuring means thereby removing the voltage difference between said electrodes and returning the sample to its ambient electrostatic state.

2. The apparatus of claim 1 wherein the measuring means comprises means for measuring the voltage across the electrodes, and the voltage measuring means comprises a voltage divider with a resistive network connected in parallel with the electrodes of the applying means and a voltage monitor for measuring a voltage of the network representative of the voltage across the electrode network.

3. The apparatus of claim 1 wherein the short-circuiting means comprises a voltage pulse generator and a spark gap device connected to the generator in parallel with the applying means, said voltage pulse generator responsive to a triggering signal from the measuring means, to create a spark across the spark gap device dissipating the voltage across the electrodes of said applying means.

4. The apparatus of claim 1 further including a means for delaying actuation of the short-circuiting means by a predetermined amount connected between the measuring means and the short-circuiting means such that a delay exists between the time that the measuring means reaches a predetermined level and the time that the electrodes of the applying means are short-circuited.

5. The apparatus of claim 3 wherein the delaying means comprises a delay generator connected between the measuring means and the short-circuiting means such that a delay exists between the time that the parameter being measured reaches a predetermined level and the time that the electrodes of the applying means are short-circuited.

6. The apparatus of claim 4 wherein the short-circuiting means comprises a voltage pulse generator and a spark gap device connected to the generator in parallel with the applying means, said voltage pulse generator responsive to a triggering signal from the measuring means, to create a spark across the spark gap device dissipating the voltage across the electrodes of said applying means.

7. The apparatus of claim 6 wherein the first of said electrodes comprises an electrically conducting member having a substantially horizontal surface in contact with the sample and wherein the second of said electrodes comprises an electrically conducting rod with its longitudinal axis lying in a plane substantially perpendicular to the plane of the horizontal surface of said first electrode and further having a tapered end adjacent the sample.

8. The apparatus of claim 7 wherein said second electrode further comprises a plexiglass plate connected to the tapered end of the rod, said plate having a horizontal surface in contact with the sample and lying in a plane substantially parallel to the plane of the horizontal edge of the first electrode.

9. The apparatus of claim 8 wherein the measuring means comprises means for measuring the voltage across the electrodes.

10. The apparatus of claim 9 wherein the voltage measuring means comprises a voltage divider with a resistive network connected in parallel with the electrodes of the applying means and a voltage monitor for measuring a voltage of the network representative of the voltage across the electrode network.

11. The apparatus of claim 10 wherein the supplying means comprises a capacitor connected through a switchable relay to either a voltage power source or said applying means, such that when connected to the power source the capacitor charges to a predetermined voltage and when connected to the applying means, discharges through the applying means supplying a voltage difference to the electrodes of said applying means.

12. The apparatus of claim 11 further comprising a current monitor for providing a signal representative of the current passing through the electrodes of the applying means.

13. The apparatus of claim 1 wherein the short-circuiting means comprises a voltage pulse generator and a spark gap device connected to the generator in parallel with the applying means, said voltage pulse generator responsive to a triggering signal from the measuring means, to create a spark across the spark gap device dissipating the voltage across the electrodes of said applying means.

14. The apparatus of claim 1 wherein the first of said electrodes comprises an electrically conducting member having a substantially horizontal surface in contact with the sample and wherein the second of said electrodes comprises an electrically conducting rod with its longitudinal axis lying in a plane substantially perpendicular to the plane of the horizontal surface of said first electrode and further having a tapered end adjacent the sample, and wherein said second electrode further comprises a plexiglass plate connected to the tapered end of the rod, said plate having a horizontal surface in contact with the sample and lying in a plane substantially parallel to the plane of the horizontal edge of the first electrode.

\* \* \* \* \*